United States Patent [19]

Foster et al.

[11] 4,444,879
[45] Apr. 24, 1984

[54] IMMUNOASSAY WITH ARTICLE HAVING SUPPORT FILM AND IMMUNOLOGICAL COUNTERPART OF ANALYTE

[75] Inventors: Terry L. Foster, Abilene; Raymond C. Casey, Baird, both of Tex.

[73] Assignee: Science Research Center, Inc., Abilene, Tex.

[21] Appl. No.: 229,448

[22] Filed: Jan. 29, 1981

[51] Int. Cl.³ .................. G01N 33/54; G01N 33/58
[52] U.S. Cl. .................................. 435/7; 422/56; 422/61; 435/805; 435/810; 436/513; 436/532; 436/810
[58] Field of Search .................. 435/5, 7, 188, 287, 435/294, 805, 810; 422/55, 56, 57, 58, 61; 23/230 B; 424/1, 8, 12; 436/532, 513

[56] References Cited

U.S. PATENT DOCUMENTS

| Re. 29,169 | 4/1977 | Schuurs et al. | 435/7 |
|---|---|---|---|
| 3,888,864 | 6/1975 | Cleeland | 436/532 |
| 3,963,441 | 6/1976 | Dietrich | 435/7 |
| 4,246,339 | 1/1981 | Cole et al. | 435/7 |
| 4,256,833 | 3/1981 | Ali et al. | 435/7 |
| 4,267,270 | 5/1981 | Stout | 435/7 |
| 4,292,403 | 9/1981 | Duermeyer | 435/7 |
| 4,299,916 | 11/1981 | Litman et al. | 435/7 |
| 4,340,564 | 7/1982 | Harte et al. | 422/56 |
| 4,357,142 | 11/1982 | Schall | 435/180 X |
| 4,363,634 | 12/1982 | Schall | 436/527 |

FOREIGN PATENT DOCUMENTS 2013337 8/1979 United Kingdom .................. 435/7

OTHER PUBLICATIONS

Chemical Abstracts I, 90:199881z, (1979).
Chemical Abstracts II, 94:188236z, (1981).

Primary Examiner—Sidney Marantz
Attorney, Agent, or Firm—Kane, Dalsimer, Kane, Sullivan and Kurucz

[57] ABSTRACT

Methods and apparatus for immunoassays. The apparatus comprises a water-insoluble article bearing a dried film of a synthetic, polymeric resin having attached chemical groups capable of forming covalent bonds with immunoreactants. The method and apparatus may be applied to determine total immunoglobulin and IgE.

9 Claims, 6 Drawing Figures

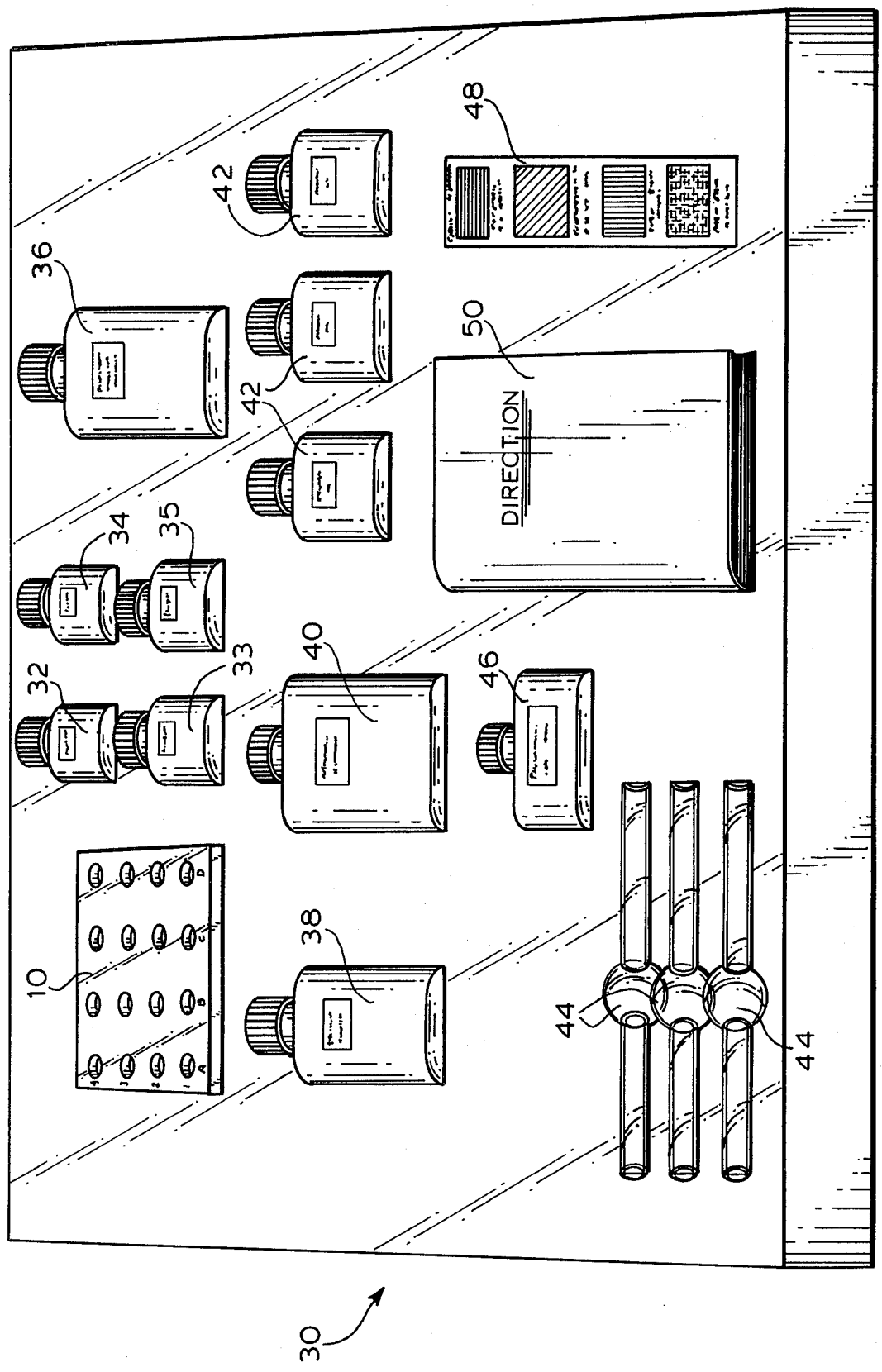

IMMUNOASSAY WITH ARTICLE HAVING SUPPORT FILM AND IMMUNOLOGICAL COUNTERPART OF ANALYTE

BACKGROUND OF THE INVENTION

1. Field of the Invention

The invention relates to the immunoassay of protein such as total and specific immunoglobulins in biological fluids and more specifically to methods and apparatus for such an immunoassay.

2. Brief Description of the Prior Art

Immunoglobulins are modified forms of the blood protein known as globulin and include antibodies and reagins. They are found in the body fluids of vertebrates following their sensitization by exposure to a protein or antigen foreign to the vertebrates evolutionary chemistry.

A wide variety of procedures are known for the immunoassay of immunoglobulins, i.e.; the determination of the quantity of immunoglobulins in a given biological fluid, using immuno-chemical technique. Immunochemistry is chemistry classically concerned with the physical interaction between "antigens" and "antibodies".

"Antigens" are high molecular weight compounds, usually protein or protein-polysaccharide complexes, which upon entry in the blood stream of a vertebrate stimulate the transformation of the small lymphocytes of the B-type into lymphoblasts. The lymphoblasts secrete antibodies specific to the antigen stimulator. The antibodies are proteins possessing reactive sites specifically complimentary to a reactive feature or site on the stimulating antigen. Antibodies generally have the property of rendering the antigen harmless to the host organism, by occupying the immunologically active sites on the antigen particles or molecules, and sometimes also by forcing precipitation or agglutination of the antigen, or by other protective mechanisms.

The words "precipitation" and "agglutination" differ in that precipitation refers to formation of a particulate or agglomerate solid from molecules initially in solution or, particularly in immunology, dissolved in blood serum. Agglutination refers to formation of an agglomerate from particulate substances initially suspended in a fluid. When suspended particles react with dissolved molecules to form an agglomerate, the term "agglutination" is usually applied. In addition, the word "agglomeration" is used as a general term encompassing both pairing of particles and clamping of a large multiplicity of particles.

In some applications it becomes difficult or meaningless to maintain the classical distinction between antigen and antibody, because in many regards the relation between antigen and antibody is reciprocal and each precipitates or agglutinates the other. The basis for the distinction resides in the history of the particular substances, and this can become irrelevant outside the original antibody-generating organism, for example in reagent applications. For this reason the antigen-antibody relationship may be advantageously described in this reciprocal way; an antibody is the "immunological homologue" of the antigen which produced it, and vice versa. An antibody and its corresponding antigen are thus homologues of each other. They may also be said to be homologous to each other.

In any event, the immunochemical antigen-antibody relationship forms the basis for immunoassay of either "homologue". Procedurally, the various known techniques of immunoassay for the immunoreactants (antigen, antibody), i.e.; radioimmunoassay, fluorescent immunoassay and enzyme immunoassay are substantially identical. Each technique comprises, in general, the separation of bound and labeled immunoreactant from unbound, labeled immunoreactant. This may be done, for example by immobilizing one of the immunoreactants, labeling one of the immunoreactants with a marker or tag to monitor its presence and reacting the immobilized immunoreactant with the free immunoreactant and measuring the degree of reaction through monitoring of the labeled immunoreactant. The difference between the various techniques resides in utilization of different reagents as markers or tags for visualization and measurement of the immunoreaction.

In the prior art immunoassay techniques, there are two principal methods for immobilizing one of the immunoreactants.

The first method of immobilization constitutes a physical adsorption or entrapment of the one immunoreactant on a water-insoluble solid such as charcoal, glass or a water-insoluble synthetic polymeric resin. The use of polymeric resins as the immobilizing substrate in the form of test tubes, microtiter plates, "dipsticks", or similar configurations is popular. The strong electrostatic charge of the resin substrate is advantageous and the procedure has proven satisfactory when measuring relatively high concentrations of unknown antigen or antibody, such as antibodies to specific infection where the antibody titers are high. However, the adsorption of immunoreagents onto plastic surfaces forms a significantly weaker bond than, for example covalent bonds. Washing steps in the procedure can often result in inaccurate or completely erroneous results by washing away the weakly bound immunoreagents. The loss of bound immunoreactant may adversely affect the immunoassay. Consider the following example:

OBJECTIVE: To determine if a patient's blood serum contains antibodies to rubella virus.

PROCEDURE:

1. Solid-phase+rubella protein (adsorbed).
2. Add patient's serum—specific antibodies react with rubella protein.
3. Wash extensively to remove extraneous immunoglobulin (IgG) in patient's serum.
4. Add labeled (radioactive, fluorescent, or enzyme) anti-Human IgG (this reacts with IgG bound to rubella protein).
5. Wash to remove unbound labeled anti-IgG.
6. Monitor radiation remaining, fluorescence emitted, or add specific substrate to monitor enzyme activity.

INTERPRETATION:

1. If the patient possesses rubella antibodies, Step 6 will produce a positive response.
2. If the patient possesses no rubella antibodies, the washing will remove all of the labeled anti-IgG and Step 6 will give a negative response.

CONSIDERATIONS: Suppose that the washing steps resulted in unexpected release of adsorbed rubella protein.

1. If this occurred in Step 2, the patient's IgG could adsorb to the solid phase substrate.
2. If this occurred to Step 3, labeled anti-IgG could adsorb to the solid phase substrate.

In both of these cases false positive reactions or false high titers would be observed.

3. If this occurred in Step 5, all proteins would be washed away. This would result in the observation of false negative reactions or false low titers.

The above-described assay generally presents no inaccuracy only when the immunochemical reactant being assayed is present in high concentrations. The losses are magnified several-fold however when the assay is to measure immunoreactants present in low concentrations.

In addition, the literature has pointed out the problems of nonspecific binding immunoreagents and unusually high response negative controls when using the adsorption procedure to immobilize immunoreactants for immunoassay procedures; see for example Sack, S. A., P. K. B. Neog:, M. D. Khorshed Alam. (1980), Immunobead Enzyme-Linked Immunosorbent Assay for Quantitating Immunoglobulin A in Human Secretions and Serum, Infection and Immunity, 12:281–283; Carlson, J., D. Gabel, E. Larsson, J. Ponten, B. Westermark (1979), Protein Coated Agarose Surface for Attachment of Cells, In Vitro, 15:844–850; and Boenisch, T. (1976). Improved Immunoassay for Trace Proteins In Proteins and Related Subjects, Protides of Biological Fluids, 24:743–749.

The second method of immobilizing an immunoreactant is by a covalent binding of the immunoreactant to a water-insoluble substrate. This is a very satisfactory method of immobilization, firmly holding the immunoreactant during washings, reaction etc. However, it will be appreciated that one is limited to the use of very specific, reactive substrates which will form a covalent bond with the immunoreactant. Representative of such substrates are diazotized polystyrene, p-aminobenzylcellulose (PAB-cellulose), isothiocyanate substituted graft copolymer of styrene and polytetrafluoroethylene and like materials. The disadvantages of such materials resides in the limited form available. For example, one of the most satisfactory of reactive solid-phase materials are the carbohydrate polymer beads and synthetic polymer beads such as agarose beads (sometimes activated with cyanogen bromide), carboxylated or aminated polyacrylamide beads and cellulose discs or particles activated with cyanogen bromide. However, these water-insoluble materials are not readily molded into forms other than beads, particles or discs and like forms. This is a disadvantage. The physical forms necessitated complicates the washing process during immunoassay in that the beads, discs or particles must be filtered, centrifuged, or allowed to settle between washes. Because of the nature of the cellulose discs and their greater absorbancy, they must be suspended in the wash solutions for an inordinately longer period of time. These are severe disadvantages when one desires rapid, efficient test procedures.

The present invention comprises a process for coating light-transparent, water-insoluble polymeric surfaces so that they remain optically clear yet become chemically reactive so that immunoreagents can be covalently bound to the surface. The light-transparent, water-insoluble polymeric resin so coated may be any of those moldable in configurations other than just beads, particles etc. (such as tubes, microtiter plates, petri dishes, and the like).

Also by the present invention, one may prepare water-insoluble surfaces normally inert to chemical reactions (glass, plastic, metal, and the like) for covalently bonding the primary immunoreagent in an immunoassay. This immunoreagent can be an antigen when the assay is for antibodies, or can be an antibody, lectin, or similar chemical when the assay is for an unknown protein or similar complex molecule.

We also describe herein a procedure for the use of the solid-phase technology described above in an immunoassay to monitor or measure total reaginic antibodies (immunoglobulin E of IgE) and/or allergen specific IgE utilizing enzyme immunoassay (EIA). Measurement of IgE is a specific case where the material to be assayed is present in extremely small concentrations (generally).

Reagins are complex organic compounds belonging to the class of immunoglobulins known as immunoglobulin E (generally referred to for convenience as "IgE"). More specifically reagins are a group of type IgE proteins found in the blood serum of vertebrates, following their sensitization by exposure to an allergen or allergens. The endogeneously produced reagin may be characterized in part by its antibody-like activity, i.e., its specific reactivity in binding at epitopic sites on the counterpart allergen which is the source of its own genesis. The reagin also generally has a propensity to attach to living cells throughout the body of the host vertebrate. When the counterpart allergen is reintroduced into the previously sensitized host vertebrate, an allergen-reagin reaction takes place usually with a consequential anaphylactoid type of immune reaction. The latter results primarily from a rupture of eosinophils having attached reagins—allergen complex. Rupture of the cells releases histamine, slow-reacting substance of anaphylaxis, eosinophil chemotaxic substance, lysosomal enzymes and other compounds which result in an allergic reaction in the host vertebrate. Allergic reactions include anaphylaxis, urticaria, hay-fever, asthma and like clinical manifestations.

To avoid allergen-reagin reactions in a sensitized vertebrate, one hopefully identifies reagins in the blood serum of the vertebrate and then precautions may be taken to limit exposure of the sensitized individual to allergens corresponding to the identified reagin or reagins or by desensitizing the individual to specific allergens.

In view of reagin-antibody activity, prior art in-vitro methods of identifying reagins in blood serum have been based, empirically, on the known and classic immunological relationship which exists between an antigen and its homologous antibody. However, such prior art methods have not been entirely satisfactory in regard to reagin identification for a number of reasons. First, allergens, which are in essence protein substances foreign to the chemistry of a given vertebrate, apparently stimulate the production of relatively small quantities of reagin in comparison for example to the production of antibody to disease antigens. The smaller production of reagin complicates its detection and identification in the complex mixture comprising blood serum.

Additionally, the majority of native allergens possess a plurality of allergenic determinants and when introduced into a vertebrate will provoke or elicit a mixed plurality of reagins instead of a single reagin. The mixture of reagins will differ from each other in their physicochemical and biological properties, complicating further identification of the reagin entity. Some of the minor compounds elicited in the mixture may be in such low concentrations that they are not detectable by conventional physicochemical techniques.

Secondly, since most IgE material isolated from host organisms has been found to be a heterogeneous mixture of structurally similar but diverse proteins, and a specific reagin may in fact be a mixture of different reagin molecules, any in-vitro detection method based on binding of the reagin with an allergen may depend for accuracy on a protocol which may not account for all of the diverse reagin molecules and not just a portion of the mixture.

In addition, it will be appreciated that since immune sera contains reagins which will bind to their corresponding allergens with varying degrees of avidity, strong positive allergen-reagin reactions may not always be obtained in reasonable times. Further, the physical nature of the reagin mixture might be expected to affect the strength of any interaction or binding of reagin which may occur.

It has also been recognized that IgE materials do not behave in the same way as, for example, IgM or IgG, the protective antibodies produced by an organism to counteract antigens related to diseases. In the latter process, the host organism may continue to produce "protective" types of antibody even after the disease state or entity has been eliminated, thereby obtaining immunity to re-infection. In contrast, in the case of allergy whose physical manifestation of the allergic response is the binding of the allergen with the reagin, no immunity is necessarily conferred. When the binding reaction occurs, cellular damage occurs wherein substances such as histamine are released to affect allergic target tissues. The binding reaction will occur during every subsequent re-introduction of allergen into the host organism.

Clearly, although there are apparent analogies between the classical immunological antigen-antibody relationship and the more specific allergen-reagin process, there are also subtle and marked differences. It is these differences which suggest that the prior art empirical use of antigen-antibody in-vitro identification procedures to identify allergens-reagins may have been misplaced and accounts for the inaccuracies which have been observed (lack of avidity, specificity) and the lack of sensitivity.

Because of the dissatisfactions with the prior art in-vitro methods of determining and identifying reagins in blood serums, the most widely employed methods of determining reagins present in the blood serum of allergen sensitized vertebrates (and thereby a differential diagnosis of atopic or anaphylactic allergy) are the in-vivo skin and provocation test methods. These in-vivo test methods are also lacking in complete satisfaction. They are time consuming, inconvenient to patients and not without serious risk. The potential for anaphylaxis upon exposure of the patient to allergens is a real hazard.

Like the prior art in-vitro methods for identifying reagins, the in-vivo methods are also inaccurate to a degree. The allergen-reagin reaction physical manifestations observed in skin-testing may be affected by subjective influences such as an allergic threshold in individual body resistance to allergic response. Emotional factors in the individual undergoing testing can also affect the allergic response.

In summary the prior art methods, both in-vitro and in-vivo, for identifying reagins in the blood sera of vertebrates have not been entirely reliable, accurate or safe for the variety of reasons described above. The method of the present invention is an improvement over the prior art methods.

There are a number of advantages associated with the method of our invention. A major advantage resides in the capability of performing allergen identification testing in the physician's office on a simple, economical and rapid basis. The use of the patient's blood serum in an in-vitro test method obviates the hazards associated with conventional skin-testing and provocation test procedures (risk of anaphylaxis). This is particularly advantageous where the very young, elderly and debilitated individual is the object of testing. Other advantages include more stable reagents with less associated hazards and which require less training in their use than those associated with, for example, the radioellergoimmunosorbent test (RAST) which employs radioactive labelled reagents. The reagents used in the method of the invention also have longer shelf-lives than radioactive labelled reagents and are safer to use.

The method of the invention also requires only relatively small blood serum samples for testing, providing the patient with considerably decreased discomfort and loss of time. Once the blood sample is obtained the patient need not wait for results. Automation of the procedure will enable the physician to increase the number of patients he can diagnose in a given time period.

Because the method of the invention measures total and specific IgE it enables the physician to monitor allergy therapy by monitoring serum IgE levels. This is a very sensitive monitor. In contra-distinction skin test results fluctuate rapidly over short periods of time depending on the physical state of the patient. The method of the invention is more consistent and repeatable than skin-testing because it comprises monitoring serum components which are less affected by the patient's physical condition.

Results of the immunoassay of the invention may be observed visually or quantitated with a simple spectrophotometer and highly sophisticated apparatus is not required.

SUMMARY OF THE INVENTION

The invention comprises a solid-phase support for immobilizing reactants of an immunoreaction, which comprises; a water-insoluble article which is inert to chemical reaction with said reactants; and a dried film of a synthetic, polymeric resin having attached chemical groups capable of forming covalent bands with the reactants, coating at least a portion of the article.

The invention also comprises the manufacture and use of the support of the invention in an immunoassay for proteins, including immunoglobulins.

The invention also comprises an immunoassay of total and allergen specific immunoglobulin E (IgE) in a biological fluid containing said IgE, which comprises;

extracting the IgE from the fluid by binding the IgE to an immobilized allergen immunological counterpart of the IgE;

complexing the bound IgE with enzyme-conjugated with anti-IgE;

mixing the complex with a chromogenic reagent capable of developing color in the presence of the enzyme; and observing the degree of color developed in the mixture.

The term "allergen specific immunoglobulin E (IgE)" as used throughout the specification and claims means the antibody-like reagin or reagins which are produced endogenously by a vertebrate in response to exposure or sensitization to a given allergen. The mechanism by which reagins are produced in response to sensitization is a matter of speculation, but the reagins or IgE may be found in the circulating blood serum and in other biological fluids associated with the sensitized individual.

The term "immobilized allergen immunological counterpart of the IgE" as used herein means anit-IgE or the specific allergen responsible for the endogenous production of the IgE material by a sensitized individual, which has been immobilized by a physical or chemical bonding to a solid, water-insoluble surface. Preferably there is a covalent chemical bond between the allergen and the water-insoluble surface as described above.

BRIEF DESCRIPTION OF THE DRAWINGS

FIG. 6 is an isometric view of an embodiment kit of the invention useful for immunoassay of immunoglobulins.

DETAILED DESCRIPTION OF THE INVENTION

Those skilled in the art will have an appreciation of the invention from a reading of the following description of the preferred embodiments thereof, when the reading is in conjunction with a viewing of the attached drawings of FIGS. 1-6, inclusive.

The description herein will be specific for the modification of chemically inert, water-insoluble polymeric resin surfaces of test tubes, cuvettes and microtiter plates. Those skilled in the art will appreciate however that the invention is not limited in scope to such embodiments. The inventors envision the modification of metals (balls, "dipsticks", beads and the like), glass, fibrous materials and similar physical materials so they may be used as chemically active substrate for immobilizing imunoreactants. Similarly, the following description is of specific embodiment antigen-antibody reactions, but the invention is not limited to these specific reactions. The invention includes for example non-immunological specific binding protein reactions in general, lectin-specific chemical reactions in general (such as Concanavalin A and n-acetylglucosamine), enzyme-enzyme conjugate reactions and like reactions for determining proteins.

Figure 1:
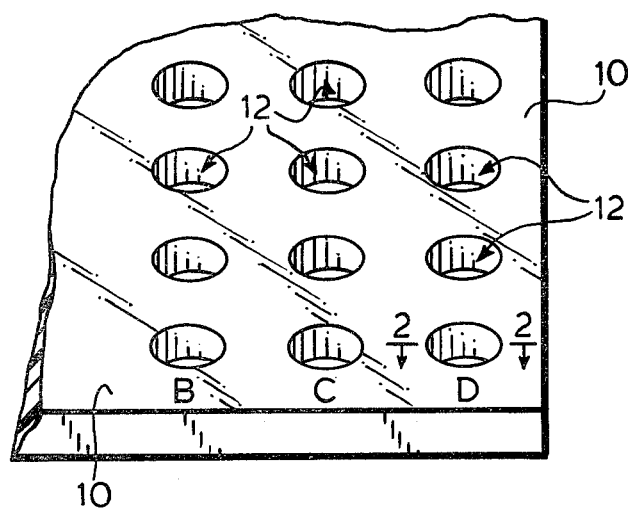
FIG. 1 is a view-in-perspective of a portion of an embodiment article (titer plate) of the invention.

FIG. 1 is a view-in-perspective of a portion of a titer plate 10 fabricated from a water-insoluble, light-transparent, synthetic polymeric resin normally inert to chemical reaction with an immunoreactant such as an immunoglobulin or its homologous immunological counterpart, anit-immunoglobulin (anti-Ig). Such resins are well-known as in their preparation and moldability into articles such as titer plate 10 or test tubes or cuvettes. Representative of such resins are polystyrene, polyacrylate, polymethacrylate, polycarbonate, poly(ethylene terephthalate), polyethylene, polypropylene, polyvinyl chloride and the like. The titer plate 10 may also be fabricated from inorganic materials meeting the criteria of water-insolubility, and inertness described above. Representative of such inorganic materials are glass, metal and the like.

As also shown in FIG. 1, the upper surface of titer plate 10 is interrupted by a plurality of individual, closed bottom, wells 12. The wells 12 are disposed geometrically in rows and columns which may be identified with indicia such as numbers or letters (letters shown in FIG. 1) to facilitate identification of individual rows or wells 12. The number of wells, their size and configuration may be selected as desired for a given immunoassay as will be described more fully hereinafter.

Figure 2:
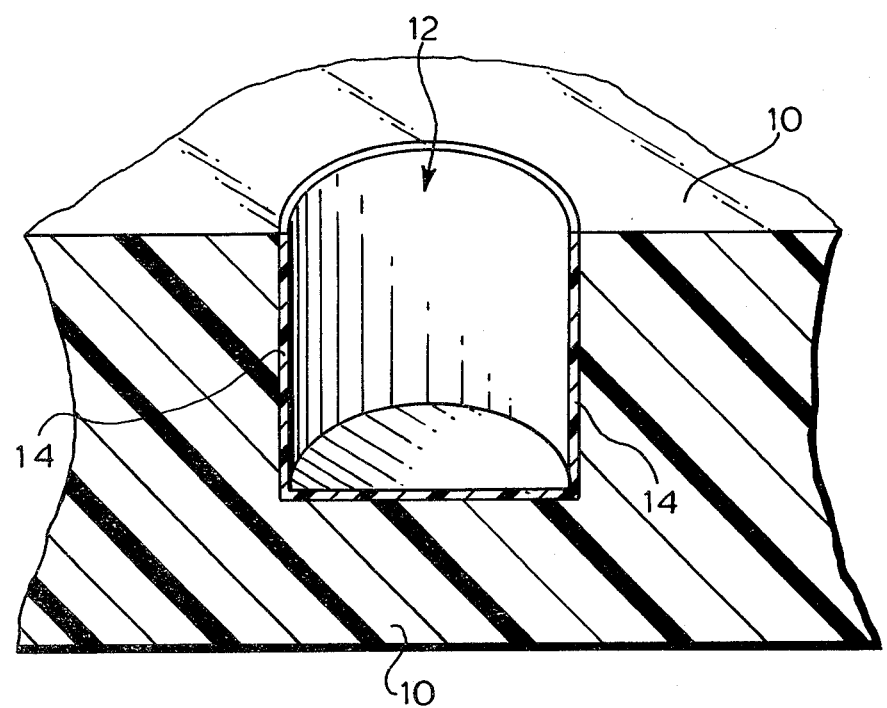
FIG. 2 is a cross-sectional side elevation viewed along lines 2—2 of FIG. 1.

FIG. 2 is a cross-sectional side elevation as viewed along lines 2—2 of FIG. 1 and shows the well 12 structure in greater detail. The inner surfaces of the well 12 bears an adherent coating of a dried film of a light-transparent, synthetic polymeric resin film 14. The film resin is one having attached chemical groups which will form covalent bonds with immunoreactants such as the immunoglobulins or the anti-immunoglobulins to be employed in the immunoassay to be carried out in the wells 12 of titer plate 10. Representative of such chemical groups are carboxyl, amino, hydroxyl, amido, mercapto, sulfhydryl and like groups attached to the polymeric chain of the resin forming film 14. Representative of such polymeric resins are acrylonitrile-butadiene-styrene copolymers, carboxylated styrene-butadiene copolymers, carboxylated ethylene polymers, carboxyl modified poly(acrylamide), poly(caprolactone) diol, carboxylated poly(vinylchloride), carboxylated vinyl chloride/vinylacetate copolymer and the like. Preferred in the method of the invention is a carboxylated styrene-butadiene copolymer such as Dow Latex 233 (Dow Chemical Corp.). The film 14 may be adhered to the wells 12 of titer plate 10 by applying the film forming resin in a liquid state and allowing it to dry in-situ.

Upon drying, the preferred polymer provides a water-insoluble, preferably optically clear surface which presents numerous carboxyl groups available for covalent attachment of the primary immunoreagent, usually a protein. If it is preferred, chemical spacer arms, such as primary amines, hydrazines, carboxlic acid anhydrides, sulfhydryl derivatives, or combinations of these and other chemicals, can be covalently bound to the free carboxyl groups prior to attachment of the immunoreagent. The spacer arms then provide the active site for binding an immunoreactant to the water-insoluble substrate. The method of application of the liquid polymer to the surface of plate 10 is determined by the specific characteristics of the surface and film 14 forming polymer and by the needs of the user. The inventors have successfully employed such techniques as baths, dips, fill and empty, and spray application techniques.

The immunoassay of the invention will determine the quantity of given protein such as immunoglobulins, including reagins, in biological fluids. The term "biological fluids" as used herein means fluids associated with a living vertebrate, such as nasal, bronchial, middle ear gastric, lachrimal and like secretion of biological origin. The immunoassay of the invention is particularly useful for determining reagin levels (IgE) in the blood serum of mammals including humans.

Figure 3:
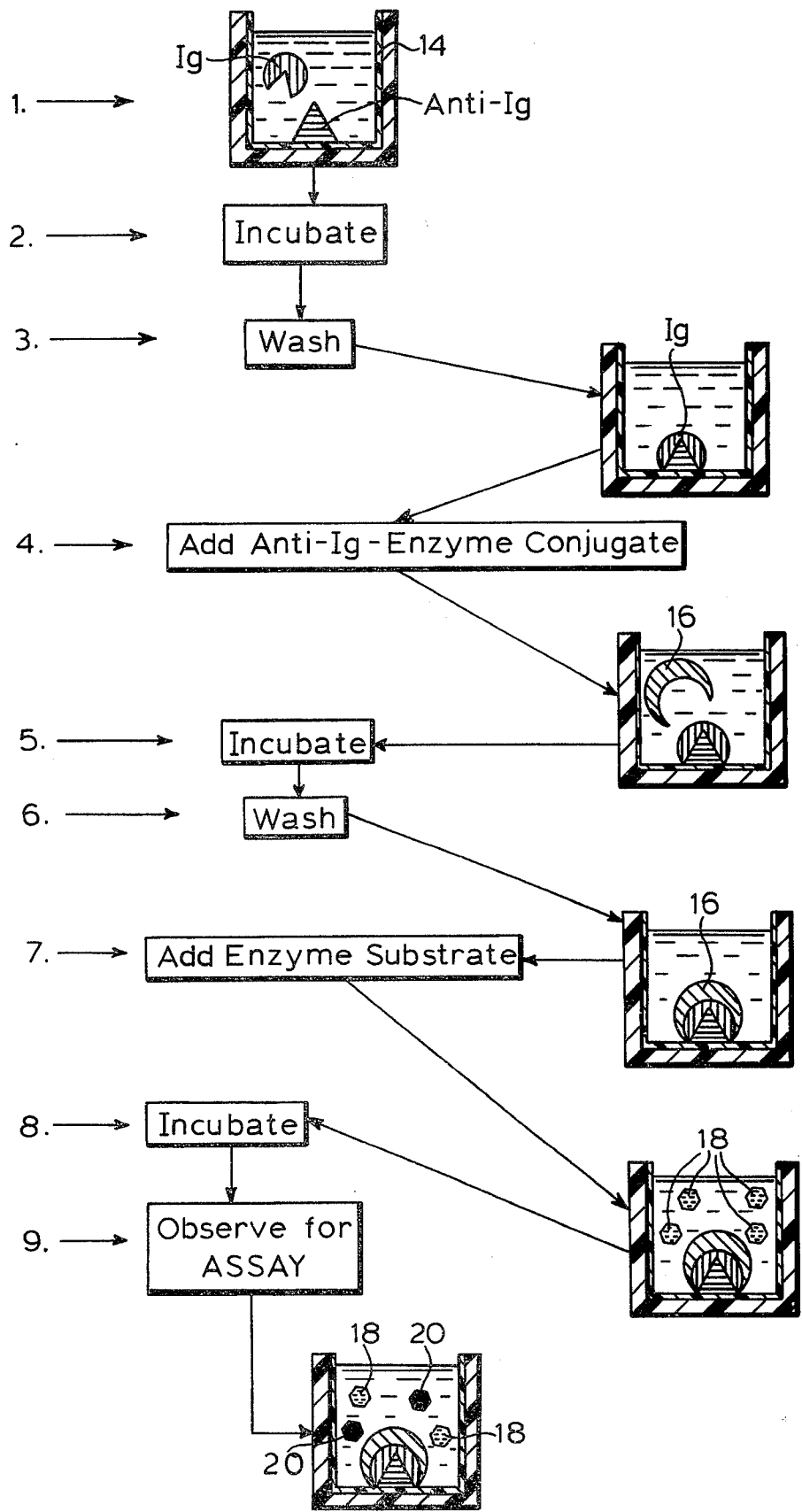
FIG. 3 is a schematic representation of an embodiment method of the invention for immunoassay of immunoglobulins employing the article of FIG. 1.
Figure 4:
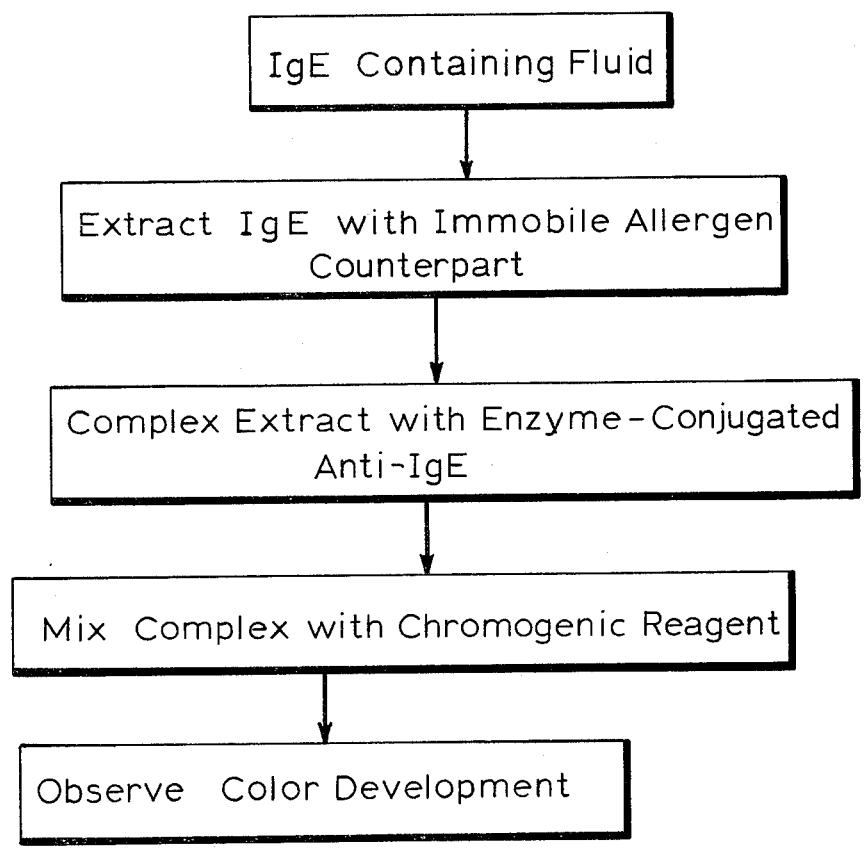
FIG. 4 is a flow diagram depicting a preferred embodiment method of the invention.

Reference is now made to FIG. 3, a schematic representation of an embodiment assay of the invention for total immunoglobulins, employing the microtiter plate 10 of FIGS. 1 and 2.

In an initial preparation, anti-Ig is covalently bound in the presence of 1-ethyl-3-(3-dimethylaminopropyl)-carbodiimide to the dry film 14 within the well 12 of microtiter plate 10 by incubating a solution of the anti-Ig in the wells 12 overnight at room temperature, removing the solution and drying the wells 12. This immunoreactant anti-Ig is thus covalently bound to the film 14.

In the step 1 shown in FIG. 3, a body fluid containing immunoglobulin (Ig) is deposited in the well 12 where the anti-Ig has been covalently bound to film 14. The deposit is incubated (2.) and then the extracted body fluid is removed leaving the extracted Ig bound, through the reaction with the immobilized anti-Ig, to the film 14. The well 12 is then washed, preferably by several rinses (3.). The extraction may be made simply by bringing together the immobilized anti-Ig, in an excess of the amount required to bind with the Ig in the biological fluid undergoing assay. The excess proportion may be calculated by trial and error technique, but one may usually employ weights of the immobilized anti-Ig equal to the weight of biological fluid undergoing assay. Advantageously, the admixture of immobilized Anti-Ig and biological fluid is incubated at a temperature within the range of from about room temperature to about 37° C. for a period of from about 0.5 to 10 hours to complete extraction, i.e.; binding of the Ig to the anti-Ig.

Following separation of the immobilized Ig/anti-Ig from the extract mixture, the bound Ig portion of the composition is complexed with an enzyme-conjugated anti-Ig compound 16 (step 4). The complex is readily formed by bringing together the two reactants, preferably in a buffer solution. Sufficient of the conjugate 16 is employed in the complexing mixture to complex with all of the Ig moiety of the immobilized Ig/anti-Ig composition. The resulting mixture is then incubated (5.) and washed (6.) as described above to obtain the complex of anti-Ig/Ig/anti-Ig-enzyme conjugate bound to film 14. The complex is generally completely formed within from about 0.5 to about 5 hours and after this period of time the complex of immobilized anti-Ig/Ig/anti-Ig-enzyme conjugate may be separated by pouring off the complexing mixture. Advantageously, the separated complex is washed (6.) with buffer solutions.

The enzyme-conjugated anti-Ig employed in the method of the invention is a conjugate of anti-Ig and any relatively stable enzyme which will conjugate with anti-Ig without loss of biological activity. The required biological activity is as a catalyst to promote development of color in a chromogenic reagent. Representative of enzymes which will conjugate with anti-Ig and remain biologically active in respect to a chromogen are the peroxidases, such as those which may be obtained from horseradish, fig leaves, potatoes and the like; and the phosphatases, especially alkaline phosphatase.

The method for preparing enzyme-anti-Ig conjugates is well-known; see for example the method of Nakane et al., Jour.Histochemistry and Cytochemistry, 22:12, page 1084.

The complex of immobilized anti-Ig/Ig/anti-Ig-enzyme is then mixed (step 7.) with a chromogenic reagent 18, the specific enzyme substrate capable of developing color in the presence of the enzyme.

The chromogen 18 employed in the method of the invention is a substance capable of undergoing a visually observable color change as a result of its specific reaction with available enzyme in the presence of an oxidizing agent such as hydrogen peroxide. Representative of chromogens 18 are redox-type indicator dyes capable of maximum color development within a specific pH range. Illustrative of such chromogens 18 are p-diphenylamine sulfonic acid, o-tolidine dihydrochloride, m-toluidine, benzidine, quaiacol, 2,7-diaminofluorene, o-dianisidine, and the like and mixtures thereof. Preferred as chromogens 18 in the method of the invention are 2,2-azino-di-(3-ethylbenzothiazoline-6-sulphonic acid) and o-phenylenediamine.

When the chromogen is mixed with hydrogen peroxide and incubated (8.) a chromogenic reagent is obtained which will turn color in the presence of the immobilized anti-Ig/Ig/anti-Ig-enzyme complex, to a degree determined by the quantity of enzyme present. The reaction which occurs may be represented schematically by the following:

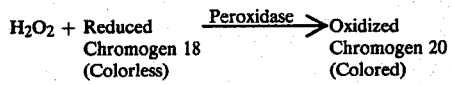

$$H_2O_2 + \text{Reduced Chromogen 18 (Colorless)} \xrightarrow{\text{Peroxidase}} \text{Oxidized Chromogen 20 (Colored)}$$

The color developed by presence of chromogen 20 can be observed (9.) visually or with the aid of a spectrophotometer or the like means of measuring color. By comparison with known standards, the quantity of Ig can be readily determined.

In the method of the invention, buffer solutions are used in wash steps 3, 6 and to dilute materials. Such buffer solutions should produce in aqueous solutions a pH value of from 6.2 to 7.5, preferably 6.5 to 7.2. A phosphate buffer (pH 7.0) is most preferred. It is also advisable to employ a urea wash following the addition of labeled antibody to insure removal of adsorbed protein. This procedure will not remove covalently bound or antigen-antibody bound protein. Follow this with a PBS pH 7.0 wash for 1 minute to allow renaturation of bound protein.

A referred embodiment process of the invention comprises the immunoassay for specific immunoglobulins, particularly reagins (IgE). The process comprises substituting specific allergens for the anti-Ig in the process shown in FIG. 3. The specific reagins are then extracted from the biological fluid in the step (1) of FIG. 3, and assayed for. The preferred immunoassay for specific IgE materials is shown in the flow diagram of FIG. 4.

The following examples and preparations describe the manner and process for making and using the invention and set forth the best mode contemplated by the inventors for carrying out the invention but are not to be construed as limiting. All parts are by weight unless otherwise specified.

EXAMPLE 1

Comparison of protein binding to untreated polymeric resin microtiter plates and carboxylated styrene-butadiene copolymer coated plates.

Polystyrene plates from different sources and one brand of polyvinylchloride plate were used for this comparison. These were 96 well plates, some with flat-bottoms, some round. The round-bottom plates facilitate a better coating with the polymer. Carboxylated sytrene-butadiene copolymer (Dow Latex 233; Dow Chemical) was added to each well and immediately withdrawn. The plates were inverted and dried for fifteen minutes at 50° C. at which time the polymer coating was observed to be optically clear.

A. In the first comparison, 50 μl of 1.0 μg/ml horseradish peroxidase (HRPO) was added to each well of treated and untreated plates. Adsorption to the untreated plates was performed in alkaline buffer of varying salt concentration and for various time periods at 4° C., 20° C. and 37° C. Covalent binding of HRPO to the polymer coating was performed in neutral buffer at room temperature for two hours. Following adsorption and covalent binding, the plates were washed in sequence as follows: 2x with pH 10.0 buffer, 2x with pH 4.0 buffer, 2x D.H$_2$O, 2x 2 M urea, 2x D.H$_2$, 2x 3 M potassium thiocyanate, 2x D.H$_2$, and finally 2x pH 7.2 phosphate buffered saline (PBS).

A standard concentration of substrate reagent [2,2'-azino-di-(3-ethyl-benzthiazoline sulphonic acid) (ABTS)] prepared as per procedures in the literature (Saunders, G. C. et al., 1978, Serologic Test Systems Development, Los Alamos Scientific Laboratory Progress Report, LA-7078-PR.) was added to the plates following each D.H$_2$O wash. Presence of HRPO is indicated by a substrate color change from green to blue and can be quantitated by reading with a spectrophotometric microtiter plate reader and comparing results to a standard curve. Following the D.H$_2$O wash after the 2x pH 4 and 10 wash, both treated (polymer coated) and untreated plates showed presence of HRPO, although the concentration of HRPO on the untreated plates was greatly reduced. All HRPO activity was removed by the thiocyanate. However, this treatment denatures protein; therefore, pH 7.2 phosphate buffered saline was added to all plates and incubated overnight to initiate renaturation of remaining protein. Addition of ABTS the next day demonstrated no HRPO on the untreated plates, whereas the polymer coated plates again exhibited HRPO activity. These results indicate removal of protein from the absorbed plate, but not from the plate wherein the protein was covalently bound.

B. In another experiment, bovine serum albumin (BSA) in concentrations of 1 mg/ml, 2 mg/ml, and 3 mg/ml was applied with constant mixing to the untreated and the polymer coated plates for two hours at room temperature. In this experiment, 1-ethyl-3-(3-dimethylaminoproyl-carbodiimide (EDAC) was included with the coated plate to facilitate covalent binding of the BSA to the carboxylated film on the plate. Following treatment with BSA, the plates were washed 3x with pH 7.2 PBS and a protein indicating reagent was added (standard method for protein assay). The untreated plates indicated no concentrations of protein. On the other hand, the polymer coated plate exhibited an indication that protein was bound to the wall plate and not free to go into solution.

C. In another experiment, we performed an enzyme innumoassay according to known procedures (NaKane, P. K. and A. Kawaoil, 1974, Peroxidase-Labeled Antibody, A New Method of Conjugation, Journal of Histochemistry Cytochemistry, 22:1084–1091) using anti-IgE, sera from allergy patients (IgE), known concentrations of IgE, and HRPO-labeled anti-IgE. The anti-IgE was adsorbed onto the surface of the untreated microtiter plates and covalently bound to the surface of the polymer coated plates. The plates were washed with appropriate wash solutions, incubated with IgE, washed, incubated with HRPO-labeled anti-IgE, washed, and the substrate was added. In this experiment, all wells should be positive; that is, should show an ABTS color change from green to blue. In the first run, no titrations were preformed, and 50 μl of the "unknown" test material (IgE) was added to each well in a concentration of 100 μg/ml. The results of this experiment are given in Table 1, below.

TABLE 1

COMPARISON OF UNTREATED AND CARBOXYLATED STYRENE-BUTADIENE COATED PLASTIC MICROTITER PLATES IN PERFORMING AN ENZYME IMMUNOASSAY FOR TOTAL IgE

| TYPE OF PLATE | TOTAL MEAN OF 100 WELLS OD READ AT 414nm | STANDARD DEVIATION |
|---|---|---|
| Cooke | | |
| Untreated | 1.424 | 0.170 |
| Polymer Coated | 1.518 | 0.168 |
| Dynatech | | |
| Untreated | 1.260 | 0.140 |
| Polymer Coated | 1.078 | 0.118 |
| Linbro | | |
| Untreated | 1.160 | 0.099 |
| Polymer Coated | 1.206 | 0.105 |
| Dynatech PVC | | |
| Untreated | 1.081 | 0.115 |
| Polymer Coated | 1.394 | 0.080 |

As can be seen from Table 1, there is little difference in the different types of plates with the Cooke plate showing the greatest optical density (greater concentration of IgE). Similarly, there is little difference between the treated and untreated plates. Results from Table 1 indicate that the polymer coated PVC plate shows the highest optical density with the least standard deviation.

Figure 5:
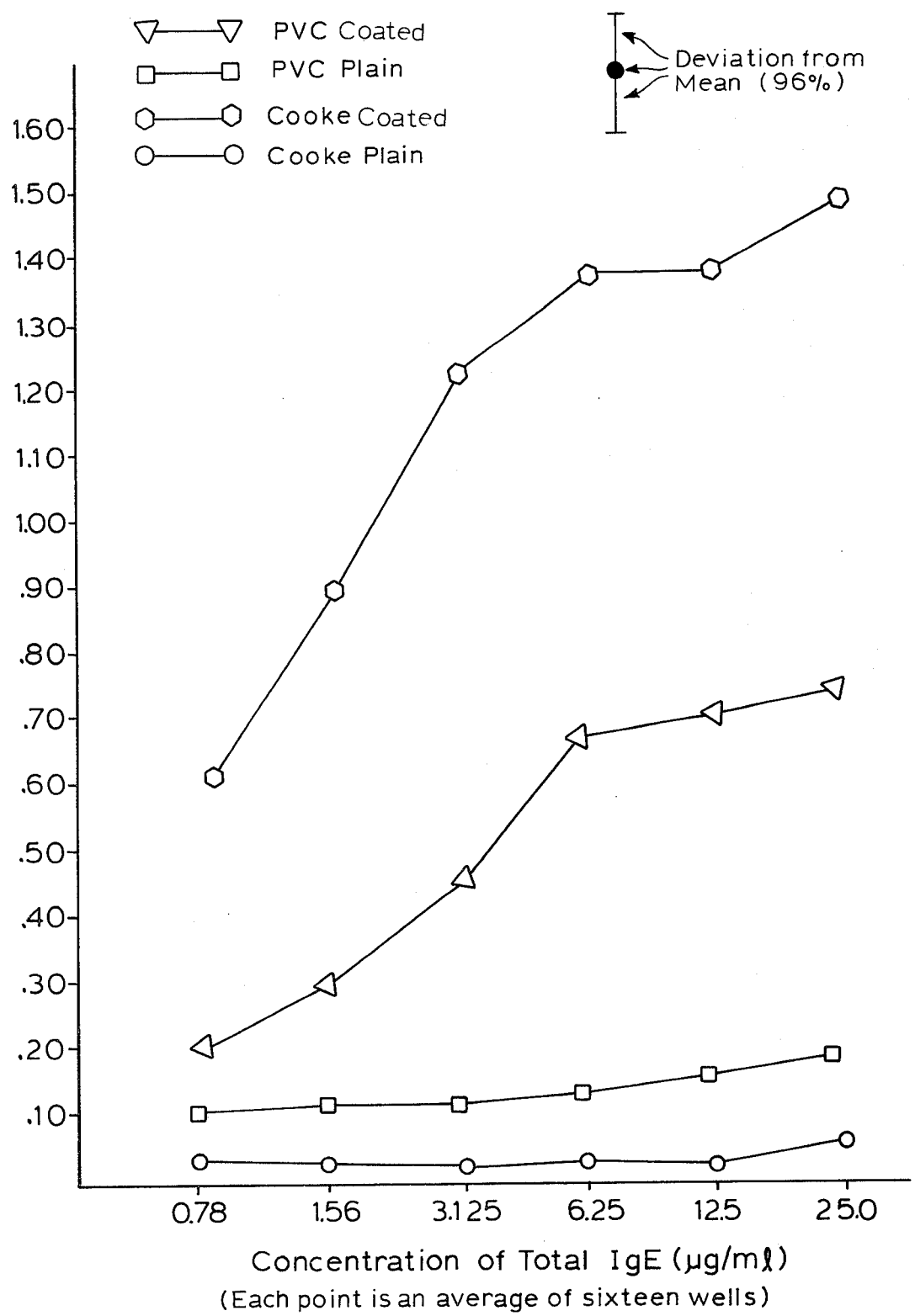
FIG. 5 is a graphical representation showing the advantage of articles of the invention such as shown in FIG. 1 compared to prior art articles.

These results were anticipated in the discussion above concerning the prior art immunoassay being adequate when the unknown being measured is present in relatively high concentrations. In a continuation of this experiment, the IgE was diluted from 25 μg to 0.78 μg, and the procedure repeated. Results as shown in FIG. 5, a graphical representation, clearly demonstrate that the polymer coated plates (covalently-bindable plates) are superior to the adsorption plate for assays. This is true with either polystyrene or polyvinylchloride (PVC) although the PVC demonstrates less variation (deviation from mean; 96%). In all cases, the untreated plates fail to detect any IgE, presenting basically a flat curve from 0.78 μg/ml to 25 μg/ml. On the other hand, all of the polymer coated plates exhibit an obvious curve of assay for decreasing concentrations of IgE.

PREPARATION 1

To an appropriate vessel there is charged 5 mg. of horseradish peroxidase dissolved in 1.0 ml of water containing 0.3 mg. of sodium bicarbonate (pH 8.1). To the charge there is added 0.1 ml. of 1 percent fluorodinitrobenzene in absolute ethanol. The resulting mixture is stirred gently at room temperature for 1 hour. At the end of this time 1.0 ml. of 0.08 M sodium periodate in distilled water is also added and stirring is continued for 30 minutes. Then, 1.0 ml. of 0.16 M ethylene glycol in distilled water is added to the resulting mixture and stirring is continued for another 30 minutes. At the end of this last period, the resulting mixture is dialyzed against 3 one-liter changes of 0.01 M sodium carbonate buffer (pH 9.5) at a temperature of 4° C. To 3.0 ml of the resulting dialyzate there is added 5 mg. of anti-IgE and the mixture is stirred gently at room temperature for 3 hours. At the end of this period, 5 mg. of sodium borohydride is added and the resulting mixture allowed to stand overnight at a temperature of 4° C. The resulting mixture is then dialyzed against phosphate buffered saline (PBS) while maintaining the mixture at a temperature of 4° C. The dialyzate is then applied to an 85×1.5 cm column of Sephadex G-200 equilibrated in phosphate buffered saline. Fractions of horseradish peroxidase/anti-IgE conjugate are collected and stored at a temperature of −20° C. in phosphate buffered saline containing 1 percent bovine serum albumin.

PREPARATION 2

An appropriate vessel is charged with 5 mls. of citrate buffer (pH 4.0). to the charge there is added with stirring 0.1 m. of a solution made by mixing 0.1 ml. of 30 percent hydrogen peroxide in 10 ml. of distilled water. To the resulting mixture there is added with stirring 0.5 ml. of a solution prepared by dissolving 200 mg. of 2,2′-azino-di-(3-ethylbenzothiazoline-6-sulphonic acid) in 10 mls. of distilled water.

EXAMPLE 2

Carboxylated styrene-butadiene copolymer is applied to fill each well of polymeric resin microtiter plates and immediately removed. The plates are inverted and dried for 15 minutes at 50° C. Allergens are extracted into solution by adding 1.0 grams of pollen, dust, or other source to 20 ml of an extraction fluid prepared as follows:

NaCl: 2.5 grams
NaHCO$_3$: 1.25 grams
Glycerin: 500 ml
D H$_2$O q.s.: 1000 ml

The extraction is carried out for 24 to 74 hours at 4° C. on a shaking machine or the material is shaken by hand approximately every hour. It is centrifuged, decanted and protein assay performed on the supernatant. Extracted allergen is incubated in the polymer-coated wells of the microtiter plate by the addition of 50-200 μl of allergen (diluted 1:10 in glycerol) to the wells. Protein concentration is critical only to the point of having sufficient allergen to saturate the walls of the wells. This is incubated for 2 hours at room temperature. Unbound allergen is washed from the wells by successive washings with PBS (pH 7.2), 0.5 M urea, PBS (pH 7.2), pH 10.0 buffer, PBS pH (pH 7.2), pH 4.0 buffer and finally PBS (pH 7.2). This rigorous washing removes allergen not covalently bound to the plate. Unreacted carboxyl groups on the plate are then blocked with a blocking agent such as ethanolamine.

The above procedure is repeated a plurality of times for each desired allergen. The arrangement of allergens in the wells is based upon the desire of the investigator. Allergens can be mixed prior to their application to the plate in such a way as to provide a screening test, say for mixed trees, mixed grasses, mixed animal danders, and the like. Also, anti-IgE can be covalently bound to the plate, the patient's serum and a standard serum diluted, the test performed, and quantitation of patient's total IgE determined.

Using the above procedure, a series of tests are made for sepcific reagins, present in the blood serum of human patients, in order to determine the allergen that the individuals are sensitive to. The results are shown below in Table 2, compared to the results obtained by use of a commercially available allergy test by radioimmunoassay and by skin-testing individuals.

TABLE 2

COMPARISON OF ALLERGY TESTING WITH A COMMERCIAL RADIOIMMUNOASSAY KIT (RIA) AND ENZYME IMMUNOASSAY (EIA)

| Patient | Total IgE RIA | EIA |
|---|---|---|
| BB | 100 | 83 |
| EB | 30 | 13 |
| JB | 32 | 3 |
| MB | 7 | 9 |
| DM | 5 | 8 |
| TR | 370 | 200 |
| TF | 15 | 8 |
| SW | 90 | 200 |
| MW | 280 | 200 |
| CS | 180 | 120 |
| JF | 26 | 10 |
| DS | 150 | 150 |
| VF | 300 | 330 |

| Patient | Allergen | Allergen-Specific IgE EIA | RIA | Skin Test |
|---|---|---|---|---|
| TR 370/200 | Bermuda | +3 | +3 | — |
|  | Orchard Grass | +2 | +1 | +1 |
|  | Perennial Rye | +1 | +1 | — |
|  | Mountain Cedar | +3 | +4 | — |
|  | Russian Thistle | +3 | +4 | +1 |
| VF 300/330 | Bermuda | +2 | +2 | — |
|  | Orchard Grass | +2 | +1 | — |
|  | Perennial Rye | +1 | +1 | +1 |
|  | Mountain Cedar | +3 | +4 | +1 |
|  | Russian Thistle | +2 | +4 | +1 |
| TF 15/8 | Bermuda | +1 | +4 | — |
|  | Orchard Grass | +1 | +1 | — |
|  | Perennial Rye | +2 | +2 | — |
|  | Mountain Cedar | +1 | +1 | +1 |
|  | Russian Thistle | +2 | +2 | — |
| CS 180/120 | Bermuda | +1 | +1 | — |
|  | Orchard Grass | +1 | +2 | +1 |
|  | Perennial Rye | +1 | +1 | — |
|  | Mountain Cedar | +3 | +3 | +1 |
|  | Russian Thistle | +1 | +1 | — |

In Table 3, the results of allergy screening by the method of the invention using the procedure of Example 2, for two human individuals, are shown in comparison to skin-tests given to the individuals.

TABLE 3

ALLERGY TEST EMPLOYING ENZYME IMMUNOASSAY

| Allergen | OD-414nm | -Blk | Rank | Skin Test | Difference |
|---|---|---|---|---|---|
| PATIENT: VF |  |  |  |  |  |
| Alternaria | .30 | .05 | +1 | +2 | 1 |
| Bermuda | .12 | .00 | 0 | +1 | 1 |
| Cat Hair | 1.31 | 1.10 | +4 | +4 | 0 |
| Cocklebur | .27 | .11 | +2 | +2 | 0 |
| Fescue | .15 | .05 | +1 | +1 | 0 |
| Johnson Grass | .19 | .06 | +1 | +2 | 1 |
| Mountain Cedar | .27 | .08 | +2 | +2 | 0 |
| Mulberry | .22 | .13 | +2 | +1 | 1 |
| Orchard Grass | .11 | .00 | 0 | +1 | 1 |
| False Ragweed | .20 | .10 | +2 | +2 | 0 |
| Giant Ragweed | .35 | .22 | +3 | +2 | 1 |
| Western Ragweed | .19 | .05 | +1 | +2 | 1 |
| Redtop | .14 | .05 | +1 | +2 | 1 |
| Russian Thistle | .20 | .06 | +1 | +2 | 1 |
| Sycamore | 1.37 | 1.13 | +4 | ND | — |
| Pigweed | .16 | .03 | +1 | +2 | 1 |
| PATIENT: TR |  |  |  |  |  |
| Alternaria | .25 | .16 | +2 | +1 | 1 |
| Bermuda | .06 | .00 | 0 | +1 | 1 |
| Careless Weed | .56 | .51 | +3 | +2 | 1 |
| Cat Hair | .11 | .02 | +1 | +1 | 0 |
| Cocklebur | .03 | .00 | 0 | +1 | 1 |
| Fescue | .04 | .00 | 0 | +1 | 1 |

TABLE 3-continued

ALLERGY TEST EMPLOYING ENZYME IMMUNOASSAY

| Allergen | OD-414nm | -Blk | Rank | Skin Test | Difference |
|---|---|---|---|---|---|
| Johnson Grass | .19 | .03 | +1 | +1 | 0 |
| Mountain Cedar | .15 | .08 | +2 | +1 | 1 |
| Mulberry | .18 | .07 | +2 | +2 | 0 |
| Orchard Grass | .05 | .00 | 0 | +2 | 2 |
| Orris Rot | .06 | .00 | 0 | +1 | 1 |

The invention also encompasses a kit for an enzyme immunoassay of the invention for the determination of immunoglobulins in test samples of body fluids. Referring to FIG. 6, there is seen an isometric view of an embodiment kit of the invention, useful for the enzyme-immunoassay of immunoglobins. The kit 30 comprises a microtiter plate 10 as previously described, a supply of various immunoglobulins 32, 33, 34 and 35 such as IgE or allergen-specific Ig-E. The kit will further contain vials 36 of appropriate buffer wash solutions or powders to be solubilized, containers 38 of enzyme-labeled anti-Ig conjugate and containers 40 of enzyme-specific substrate. Containers 42 of both positive and negative controls and a known standard specimen of Ig for quantitation are also provided. Pipettes 44 for the transfer of fluids are conveniently included, a chromogen developer solution 46 and of course a book of instructions 50 for carrying out the immunoassay of the invention. A chart 48 may be provided for comparisons to determine visually color development in the final assay step. The procedure for the use of the Kit 30 may be given in the instructions 50 as follows.

To each appropriately labeled well of the coated plate 10, to which there has been covalently bound Anti-Ig, add 50 microliters of either blank solution, standard solution, or undiluted patient sera. Incubate three hours at room temperature (23°–25° C.). Then wash plate three times with phosphate buffered saline (PBS) to which has been added 0.1% Tween 20. Tap the plate dry on an absorbant pad and add 50 μl of an appropriate dilution of Anti-Ig enzyme conjugate. Incubate three hours at room temperature and wash as before with the exception of the use of 1.0 M urea in phosphate buffered saline in the second wash followed and preceded by PBS washes. Add 50 microliters of enzyme substrate and incubate one hour at room temperature. Determine optical density at 414 nm, subtract blanks, and then compare to standards or visually access ranking for qualitative results.

We claim:

1. An immunoassay of total immunoglobulin (Ig) in a biological fluid containing said Ig, which comprises;
    extracting the Ig from the fluid by binding the Ig to an immobilized immunological counterpart of the Ig wherein the immunological counterpart of the Ig is immobilized by a covalent bonding to a dried film of a light-transparent, synthetic, polymeric resin having attached chemical groups capable of forming covalent bonds with the immunological counterpart; said film being a coating on a water-insoluble, light transparent synthetic, organic polymer article which is inert to chemical reaction with immunoglobulin (Ig);
    complexing the bound Ig with enzyme-conjugated anti-Ig;
    mixing the complex with a chromogenic reagent capable of developing color in the presence of the enzyme; and
    observing the degree of color developed in the mixture.

2. The immunoassay of claim 1 wherein the immunological counterpart is a compound selected from the group consisting of proteins, lipids, and carbohydrates.

3. The immunoassay of claim 1 wherein the chemical group is selected from the group consisting of carboxyl, amino, sulfhydryl, amido, mercapto, and hydroxyl groups.

4. The immunoassay of claim 1 wherein the resin is a light-transparent film of carboxylated styrene-butadiene copolymer.

5. An immunoassay of an allergen specific immunoglobulin E (IgE) in a biological fluid containing said IgE, which consists essentially of;
    extracting the IgE from the fluid by binding the IgE to an immobilized allergen immunological counterpart of the IgE, wherein the immunological counterpart of the IgE is immobilized by a covalent bonding to the dried film of a light-transparent, synthetic, polymeric resin having attached chemical groups capable of forming covalent bonds with the immunological counterpart; said film being a coating on a water-insoluble, light-transparent, synthetic organic polymer article which is inert to chemical reaction with immunoglobulin E (IgE);
    complexing the bound IgE with enzyme-conjugated anti-IgE;
    mixing the complex with a chromogenic reagent capable of developing color in the presence of the enzyme; and
    observing the degree of color developed in the mixture.

6. The immunoassay of claim 5 wherein the resin is a light-transparent copolymer of carboxylated styrene-butadiene.

7. The immunoassay of claim 6 wherein said fluid is blood serum.

8. An article for immobilizing reactants of an immunoreaction comprising:
    (a) a solid-phase, water-insoluble, light-transparent support made of a synthetic, organic polymeric resin;
    (b) a dried film of light-transparent, carboxylated styrene-butadiene copolymer adhering to the support of (a); and
    (c) an immuno-active composition covalently immobilized to the film of (b).

9. An immunoassay of an allergen specific immunoglobulin E (IgE) in a biological fluid containing said IgE, which comprises;
    extracting the IgE from the fluid by binding the IgE to an immobilized allergen immunological counterpart of the IgE, said immobilized allergen being covalently bound to a film of a light-transparent carboxylated copolymer of styrene-butadiene disposed on the sidewall of a light-transparent well in a titer plate fabricated from a synthetic, organic polymeric resin;
    complexing the bound IgE with enzyme-conjugated anti-IgE;
    mixing the complex with a chromogenic reagent capable of developing color in the presence of the enzyme; and
    observing the degree of color developed in the mixture.

* * * * *

UNITED STATES PATENT AND TRADEMARK OFFICE
CERTIFICATE OF CORRECTION

PATENT NO. : 4,444,879
DATED : April 24, 1984
INVENTOR(S) : Terry L. Foster and Raymond C. Casey It is certified that error appears in the above-identified patent and that said Letters Patent is hereby corrected as shown below:

Col. 6, line 13; "radioellergo-" should read -- radioallergo- --

Col. 6, line 47; "bands" should read -- bonds --

Col. 7, line 64; "as is" should read -- as in --

Col. 10, line 64; "sytrene" should read -- styrene --

Col. 11, line 54; "innumoassay" should read -- immunoassay --

Col. 15, line 17; "immunoglobins" should read -- immunoglobulins --

Signed and Sealed this

Eleventh Day of December 1984

[SEAL]

Attest:

GERALD J. MOSSINGHOFF

Attesting Officer

Commissioner of Patents and Trademarks